United States Patent [19]

Roucher, Jr.

[11] Patent Number: 5,645,789
[45] Date of Patent: Jul. 8, 1997

[54] DISTENSIBLE PET BALLOON AND METHOD OF MANUFACTURE

[75] Inventor: Leo R. Roucher, Jr., Escondido, Calif.

[73] Assignee: Navius Corporation, San Diego, Calif.

[21] Appl. No.: 504,537

[22] Filed: Jul. 20, 1995

[51] Int. Cl.$^6$ .................... B29C 49/08; B29C 49/18
[52] U.S. Cl. .................. 264/529; 264/905; 604/96; 606/194
[58] Field of Search .................. 264/523, 529, 264/530, 532, 573, 905; 604/96; 606/194

[56] References Cited

U.S. PATENT DOCUMENTS

| | | |
|---|---|---|
| Re. 33,561 | 3/1991 | Levy . |
| 3,088,173 | 5/1963 | Jones . |
| 3,141,912 | 7/1964 | Goldman et al. . |
| 3,432,591 | 3/1969 | Heffelfinger . |
| 3,627,579 | 12/1971 | Heffelfinger . |
| 4,093,484 | 6/1978 | Harrison et al. . |
| 4,141,364 | 2/1979 | Schultze . |
| 4,154,244 | 5/1979 | Becker er al. . |
| 4,254,774 | 3/1981 | Boretos . |
| 4,456,000 | 6/1984 | Schjeldahl et al. . |
| 4,490,421 | 12/1984 | Levy . |
| 4,587,975 | 5/1986 | Salo et al. . |
| 4,646,742 | 3/1987 | Packard et al. . |
| 4,681,110 | 7/1987 | Wiktor . |
| 4,702,252 | 10/1987 | Brooks et al. . |
| 4,732,152 | 3/1988 | Wallsten et al. . |
| 4,733,665 | 3/1988 | Palmaz . |
| 4,739,762 | 4/1988 | Palmaz . |
| 4,744,366 | 5/1988 | Jang . |
| 4,776,337 | 10/1988 | Palmaz . |
| 4,795,458 | 1/1989 | Regan . |
| 4,800,882 | 1/1989 | Gianturco . |
| 4,820,349 | 4/1989 | Saab ................................ 604/96 |
| 4,878,906 | 11/1989 | Lindemann et al. . |
| 4,886,062 | 12/1989 | Wiktor . |
| 4,913,141 | 4/1990 | Hillstead . |
| 4,952,357 | 8/1990 | Euteneuer . |
| 4,969,458 | 11/1990 | Wiktor . |
| 5,223,205 | 6/1993 | Jackowski et al. ............ 264/530 |
| 5,334,146 | 8/1994 | Ozasa ............................ 604/96 |
| 5,344,401 | 9/1994 | Radisch et al. . |
| 5,456,666 | 10/1995 | Campbell et al. ............ 604/96 |

FOREIGN PATENT DOCUMENTS

| | | |
|---|---|---|
| 457456 | 11/1991 | European Pat. Off. . |
| 92/08512 | 5/1992 | WIPO . |

OTHER PUBLICATIONS

Prof. Raymond B. Seymour, *The Narrowing Field of Plastics for Blow Molded Beverage Containers*, pp. 61–65, Jun. 1977, Plastics Design & Processing.

Daniel D. Ray et al., *Here's Why Polyethylene Terephthalate is the Major Competitor for Beverage Container Applications*, pp. 47–50, Sep. 1977, Plastics Design & Processing.

C. Shriver, *How to Reheat Blow Mold PET Soft–Drink Bottles*, pp. 91–93, Oct. 1977.

R.B. Frederickson et al., *Stretch–Blow Molding for Packaging Versatility*, pp. 22–26, Nov. 1979, Plastics Design & Processing.

G.S. Kirschenbaum and J.M. Rhodes, *Thermoplastic polyester:PET*, pp. 50–51, Modern Plastics Encyclopedia 1981–1982.

*Primary Examiner*—Catherine Timm
*Attorney, Agent, or Firm*—Nydegger & Associates

[57] ABSTRACT

A semi-compliant PET balloon and a method for manufacturing the balloon are disclosed. The method for manufacturing the semi-compliant PET balloon includes the steps of varying the temperature and inflation pressure on a tube of PET material in an ordered sequence to i) form the balloon, ii) thin the walls of the balloon, ii) size the balloon and then, iv) crystallize the PET material of the balloon. First, to form the balloon, the tube of PET material is preheated, and simultaneously pressurized and stretched. The pressure in the tube is then increased to conform the balloon to the shape of a mold. Next the balloon walls are thinned by decreasing pressure and providing additional stretch on the PET tube. A subsequent increase in pressure sizes the balloon. The sized balloon is next subjected to an increase in temperature and a decrease in pressure to crystallize the PET material. A cooling step completes the method for manufacture.

18 Claims, 2 Drawing Sheets

DISTENSIBLE PET BALLOON AND METHOD OF MANUFACTURE

FIELD OF THE INVENTION

The present invention pertains generally to methods for manufacturing polyethylene terephthalate (PET) balloons. More specifically, the present invention pertains to the manufacture of semi-compliant PET balloons which can be selectively inflatable to achieve a predictable balloon size. The present invention is particularly, but not exclusively, useful as a stent delivery balloon which can be manipulated to position and anchor a stent in the artery of a patient.

BACKGROUND OF THE INVENTION

Polyethylene terephthalate (PET) is a widely used material for the manufacture of balloon-type medical devices where a "non-compliant" balloon is required. Unlike "compliant" balloons, which continue to expand as internal pressure in the balloon is increased, a "non-compliant" balloon will attain and maintain a substantially constant configuration regardless of the internal pressure. For an analogy in a non-medical field, the typical party balloon is an example of a compliant balloon which continues to expand as it is being blown up. In fact, such a balloon will generally continue expanding under increased pressure until it bursts. On the other hand, a hot air balloon can not be compliant. In order to be safe and effective for its intended use, a hot air balloon must generally maintain its predetermined configuration once it has been inflated. Therefore, it is properly considered as an example of a non-compliant balloon.

In the medical field, depending on the particular application or use, it may be preferable to use either a compliant balloon or a non-compliant balloon. It happens, however, that for some medical procedures and applications it may be preferable to use a balloon which is neither typically compliant nor typically non-compliant. Such a balloon is subsequently referred to herein as being a "semi-compliant" balloon.

A well known use in the medical device field for non-compliant inflatable balloons involves the performance of angioplasty procedures. When used for this purpose, the balloon is first positioned across a stenosis in an artery. It is then inflated under relatively great pressure to a final balloon configuration to dilate the artery. The object is to use the predictable final configuration of the non-compliant balloon to dilate the artery to only a known extent. This, of course, will also breakup the plaque which is causing the stenosis in the artery and, thereby allow for the subsequent flow of blood through the previously blocked artery. Importantly, the balloon can not assume an uncontrolled or unpredictable configuration when inflated. This is so because, if left unchecked, the balloon could cause unwanted damage to the arterial system. A balloon intended for such use is disclosed in U.S. Pat. No. Re. 33,561 Which issued to Levy for an invention entitled "Balloon and Manufacture Thereof".

Use of balloons for stent placement is typically done in situations where it is necessary that a stent act as a structural support for the arterial wall in order to prevent a restenosis or collapse of the artery. The placement of a stent in an artery, however, can be an extremely complicated procedure due to the fact that arteries typically do not have constant diameter lumens and, instead, typically have arteries whose diameters vary significantly over even short distances.

Not surprisingly, the placement of a stent in an artery requires skill and dexterity. Specifically, when placing a stent in an artery it is necessary to generate forces which can be applied to various parts of the stent over controllable and predictable distances to shape and conform the stent to the artery. This, of course, must all be done in situ. Thus, a truly non-compliant balloon which has a fixed inflated configuration would be inefficient because of its inability to vary in configuration during sizing and placement of a stent. On the other hand, a truly compliant balloon would also be inefficient due to its tendency to reconfigure itself into areas of least resistance and, thereby, not necessarily apply forces at the required locations on the stent.

In light of the above it is an object of the present invention to provide a method for manufacturing and using a semi-compliant PET balloon which will expand into predictable configurations that correspond to selectively controlled inflation pressures. It is another object of the present invention to provide a method for manufacturing and using a semi-compliant PET balloon which can be manipulated in an artery and inflated to position, configure and anchor a stent into the arterial wall to prevent collapse of the arterial wall. Still another object of the present invention is to provide a method for manufacturing and using a semi-compliant PET balloon which is simple to employ, and relatively cost effective.

SUMMARY OF THE INVENTION

A method for manufacturing a semi-compliant PET balloon in accordance with the present invention includes the initial step of positioning a 20 mm. portion of an approximately 12 in. long tube of PET material in a mold. The tube is then preheated to a temperature of approximately 186° F. to soften the PET material. Next, the lumen of the PET tube is pressurized to approximately 100 pounds per square inch (psi) and, depending on the particular thickness needed for the walls of the balloon, the tube is simultaneously stretched through a distance of between 10–80 mm.

After the PET tube has been preheated, initially pressurized, and stretched, the semi-compliant PET balloon is then formed. The forming is done by increasing pressure in the lumen of the PET balloon to approximately 320 psi and maintaining that pressure for about ten seconds. This step effectively causes the PET material of the tube to conform to the shape of the mold.

Once the semi-compliant PET balloon has been formed, the walls of the balloon are thinned. To do this, the pressure inside the balloon is decreased to approximately 35 psi and, over a time interval of approximately 5 seconds, the PET tube is stretched an additional 3–10 mm.

A final sizing of the semi-compliant PET balloon is accomplished by increasing the pressure in the lumen of the balloon to around 320 psi and holding this pressure for about ten seconds.

After the balloon has been properly formed and sized, the remaining steps of the procedure are focused on preparation of the PET material itself. This involves both a crystallizing step and a cooling step. First, to crystallize the PET material of the balloon, the pressure in the formed balloon is decreased to around 100 psi. At the same time the temperature of the PET material of the balloon is raised to approximately 275° F. and maintained at that temperature for around 60 seconds. With the PET material now crystallized, the balloon is cooled at a temperature of about 85° F. and under a pressure of 100 psi for approximately 40 seconds. The final balloon product is then removed from the mold.

The result is a semi-compliant PET balloon which is capable of attaining predictable configurations under selectively variable inflation pressures. For example, for selected internal inflation pressures in the range of from 3 to 20 atmospheres (ATM), the distension size of the outside diameter of the manufactured semi-compliant PET balloon of the present invention will predictably increase at least by five percent (5%), and in one embodiment through a range of 3.2 mm to 3.8 mm.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENTS

Figure 1:
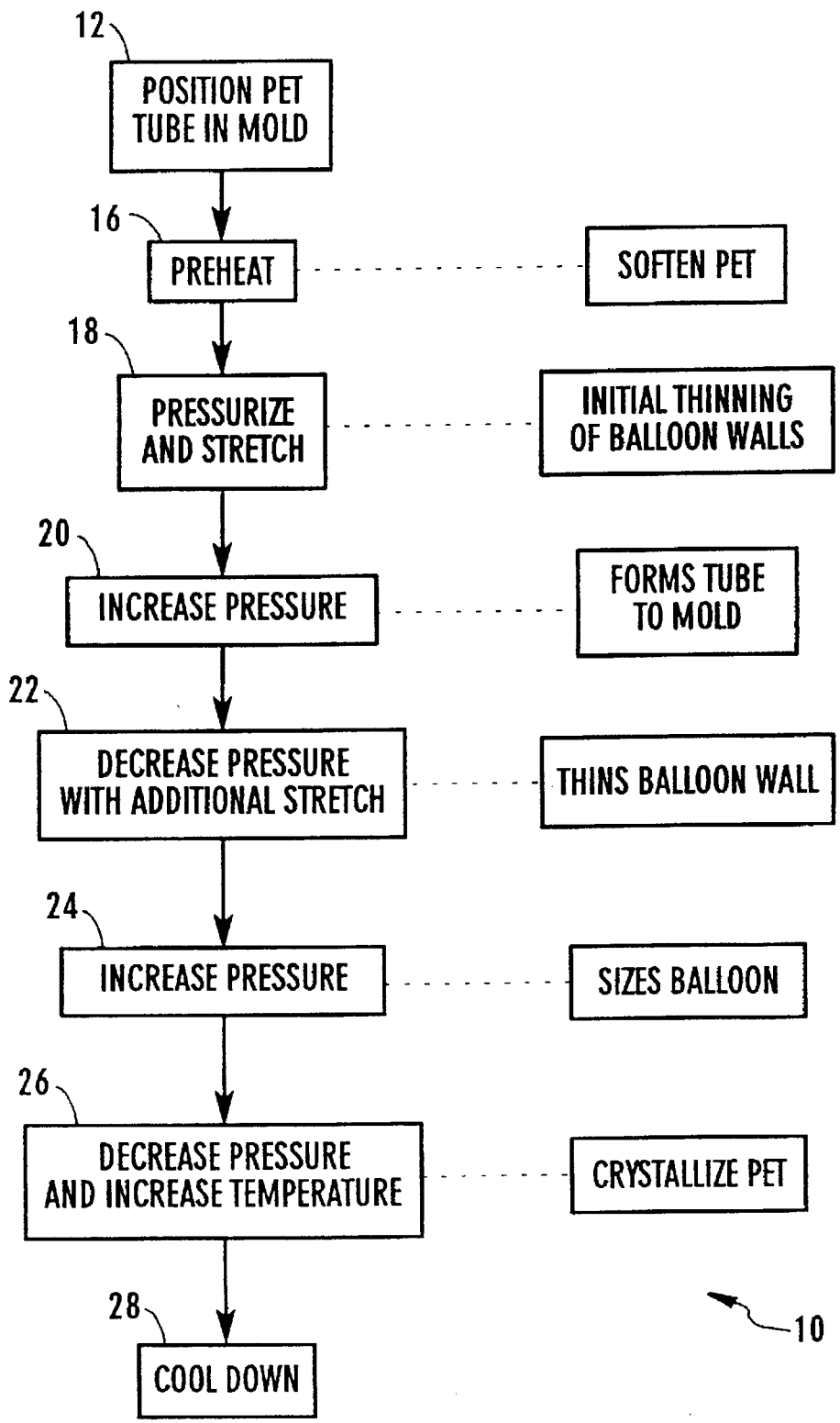
FIG. 1 is a block diagram showing the interrelation between the procedural steps of the present invention and the functional results obtained during the salient steps.

Referring initially to FIG. 1, the method and steps for performing the manufacturing process of the present invention are shown in block diagram and collectively designated with the numeral 10. As indicated by block 12, the first step of method 10 is to position a tube of PET material into a mold. For purposes of the present invention, the PET material for the tubing can be made from a raw material having intrinsic viscosities in a range of about 0.72 to 0.84. Specifically, Shell Traytuf 8456 (intrinsic viscosity 0.84), Shell Cleartuf 8006 (intrinsic viscosity 0.80), and Shell Cleartuf 7202 (intrinsic viscosity 0.72) are all suitable PET materials for use with the present invention. From these raw materials, PET tubes can be extruded using known methods which have respective intrinsic viscosities of approximately 0.78, 0.74 and 0.66. The point is that since intrinsic viscosities indirectly indicate the molecular length of the polymer in the material, and since stronger materials have higher intrinsic viscosities, the semi-compliant PET balloon of the present invention should not be made of the stronger PET materials, such as those having intrinsic viscosities above 1.0.

Although the mold that is to be used for the manufacture of semi-compliant PET balloons according to the present invention is not shown, it is to be understood that a suitable mold can be of any standard type well known in the industry which has the dimensional configuration desired for the inflated final product. Thus, by way of example only, the discussion here will consider a mold which is dimensioned to manufacture the balloon 14 shown in FIG. 2.

Returning to FIG. 1 it will be seen at block 16 of method 10 that after the PET tubing has been placed into the mold it is to be preheated to soften the PET material. Specifically, the PET material in the mold is heated to approximately one hundred and eighty six degrees Fahrenheit (186° F.). Once the material has been preheated, an initial pressurizing and stretching cycle is performed as indicated at block 18. This involves increasing pressure in the lumen of the PET tube to a pressure of approximately one hundred pounds per square inch (100 psi) and simultaneously stretching the tube through a predetermined distance. Specifically, and again by way of example only, when beginning with a PET tube having an overall initial length of around twelve inches (12 in.) the tube is drawn between thirty and eighty millimeters (30–80 mm). With step 18, the PET material in the tube is thinned while the internal pressure serves to support the walls against collapse.

The next step in method 10 involves actually forming the balloon 14. For the present invention, the forming of balloon 14 involves both pressurizing and stretching the PET material. Specifically, once the walls of the balloon 14 have been initially stretched and thinned, the pressure inside the lumen of balloon 14 is increased to approximately three hundred and twenty psi (320 psi), and this pressure is maintained for approximately ten seconds. This step is shown in FIG. 1 for method 10 by the block 20.

Block 22 of method 10, indicates that after the balloon 14 has been initially formed, the walls are further thinned. This thinning is accomplished after the pressure in balloon 14 is reduced to approximately thirty five psi (35 psi) and held for about five seconds. Specifically, this additional thinning of the walls of balloon 14 is accomplished by creating an additional stretch on the PET tube through a distance of between three and ten millimeters (3–10 mm).

A final sizing of the balloon 14, as indicated by block 24 in FIG. 1, is accomplished by another increase in pressure on the balloon 14. Again, the pressure on balloon 14 is increased to approximately three hundred and twenty psi (320 psi). As before, the balloon 14 is held at this pressure for approximately ten seconds.

From this point on in the method 10 of the present invention, the actual dimensions of the resultant balloon 14 have been established and the steps of method 10 are focused on properly preparing the actual PET material of balloon 14 for its intended use. To do this, the PET material of balloon 14 needs to be crystallized and cooled. To crystallize the PET material of balloon 14, the pressure in balloon 14 is decreased to around one hundred psi (100 psi) and the temperature of the PET material is raised to approximately two hundred and seventy five degrees Fahrenheit (275° F.). The balloon 14 is then held under these conditions (e.g. 100 psi and 275° F.) for around sixty seconds in order to properly crystallize the PET material of balloon 14. This process, shown by block 26 in FIG. 1, is then followed by a cooling step which is indicated at block 28. The cooling step 28 is accomplished for the present invention by reducing the temperature of the PET material to around eighty five degrees Fahrenheit (85° F.), and by reducing the pressure in balloon 14 to around one hundred psi (100 psi). The balloon is then cooled under these conditions for around forty seconds (40 sec).

Figure 2:
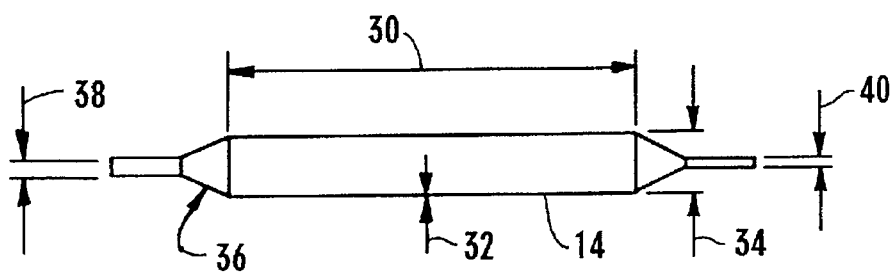
FIG. 2 is a side elevational view of a semi-compliant balloon manufactured in accordance with the steps shown in FIG. 1.

The result of all this is a balloon 14 as shown in FIG. 2 which, by way of example when considering a 3.25 mm balloon, has a length 30 of about twenty millimeters (20 mm), a wall thickness 32 less than one thousandth of an inch (0.00085 inches), and an initial outside diameter 34 of around three and one quarter millimeters (3.25 mm or 0.128 inches). The amount of taper 36 which is provided at the proximal and distal ends of the balloon 14 is largely a matter of preference, as are the diameters 38 and 40 of the tubing which extends for the respective proximal and distal ends of the balloon 14. Indeed, all dimensions of the balloon 14 can be varied according to the desires and needs of the user. In each case, however, the general procedural steps in preparing the PET material of balloon 14 are applicable.

Figure 3:
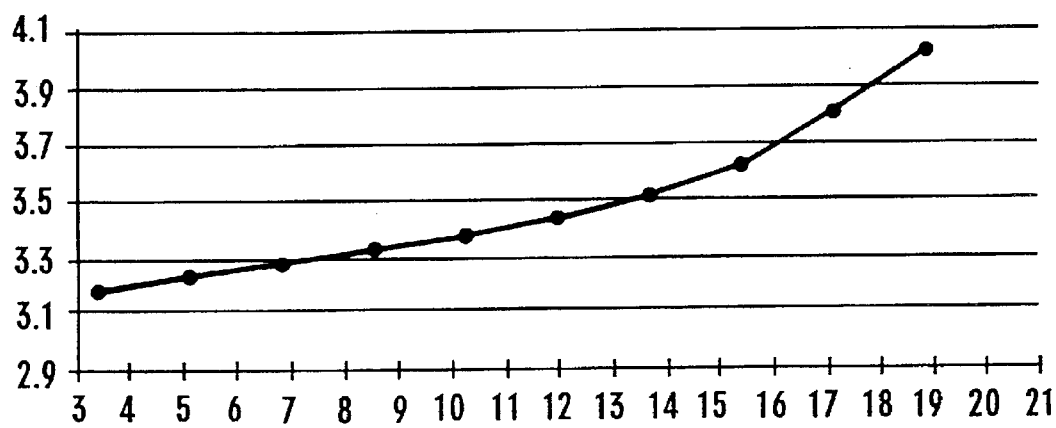
FIG. 3 is an exemplary graph which shows the variation of balloon size in distension in accordance with variations in the internal pressure of the balloon.

Upon completion of the method 10 according to the present invention, and regardless of the particular dimensions chosen for the manufacture of balloon 14, it is the purpose and intent of the present invention to provide a balloon 14 which is semi-compliant in the sense that its configuration can be changed in a predictable manner. More specifically, it is important that increases of at least 0.25 mm. in the diameter 34 of balloon 14 be accomplished with increases in internal pressure on the balloon 14 without any other significant change in the configuration of balloon 14 being realized. Indeed, in accordance with the present invention, an exemplary balloon 14 is producible which will experience changes in diameter 34 according to changes in internal pressure as shown by the graph of FIG. 3.

Figure 4:
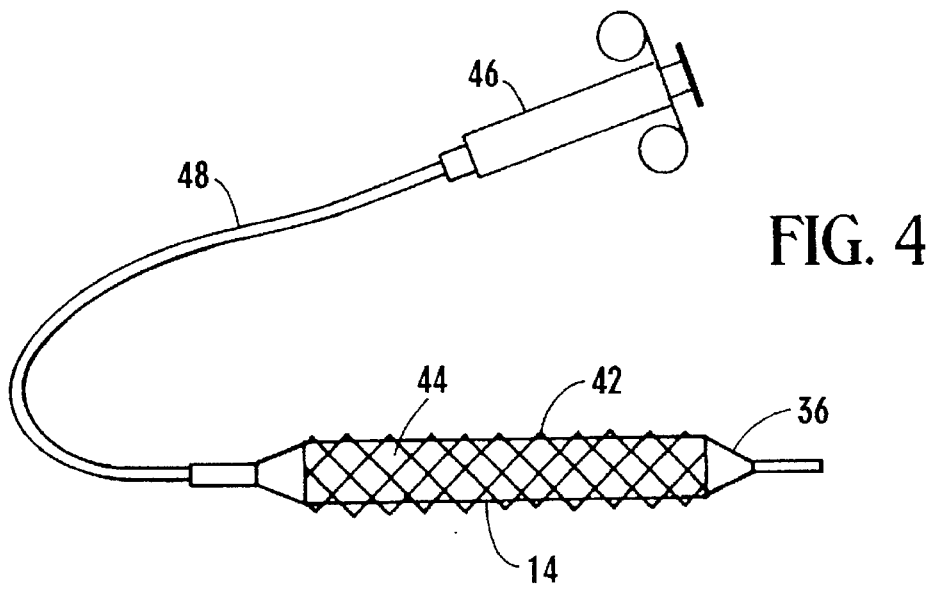
FIG. 4 is a side elevational view of a semi-compliant balloon manufactured in accordance with the present invention, with a stent installed thereon and expanded.

FIG. 4 shows a balloon 14 according to the present invention with a stent 42 installed thereon. As discussed above, the stent 42 is initially installed on the balloon 14 when the balloon 14 is deflated. At that time, the stent 42 has a relatively small unexpanded diameter. The stent 42 can be crimped onto the balloon 14 to hold it in place. After the balloon 14 and the stent 42 are advanced to the lesion in the artery, the balloon 14 is expanded as described above to expand the stent 42 to the desired diameter.

Pressurization of the balloon 14 to achieve expansion can be accomplished by fluid pressurization means such as a syringe 46 connected to the proximal end of the catheter 48. Other known pressurization means can be used as well, including any desired pressure instrumentation. The proximal end of the balloon 14 is attached to the distal end of the catheter 48. Upon pressurization of the balloon 14 to a first inflation pressure, the substantially cylindrical body portion 44 of the balloon 14 expands to a first inflated diameter, at which the balloon first achieves a fully cylindrical shape, to initially expand the stent 42. The first inflation pressure typically ranges between zero and approximately three atmospheres. At this pressure, the balloon 14 is fully inflated to a cylindrical shape but substantially undistended, and a typical first inflated diameter of the balloon 14 would be between one-and-one-half and six millimeters.

If desired, the balloon 14 can be pressurized to a second inflation pressure, to expand and distend the cylindrical body portion 44 to a second inflated diameter, to further expand the stent 42. The second inflation pressure typically ranges between three and approximately twenty atmospheres. At this pressure, the balloon 14 is typically distended to a predetermined diameter which is directly proportional to the pressure. The total change in the balloon diameter achieved by pressurizing in this range is at least five percent (5%) above the first inflated diameter. Indeed, one exemplary balloon will experience changes in diameter 34 according to changes in internal pressure as shown by the graph of FIG. 3.

After expansion of the stent 42 to the desired diameter, the balloon 14 is deflated, releasing the stent 42 from the balloon 14. The stent 42 will remain expanded in place in the lesion. The balloon 14 and the catheter 48 can then be withdrawn from the artery.

While the particular Distensible PET Balloon as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A method for manufacturing a semi-compliant polyethylene terephthalate (PET) balloon which comprises the steps of:

positioning a tube of PET material across a mold cavity, said tube having a lumen extending therethrough;

preheating said tube in said cavity to a first temperature to soften said PET material;

pressurizing said lumen to a first pressure;

stretching said tube a first predetermined distance to lengthen said tube;

forming said balloon by raising said first pressure to a second pressure;

thinning said balloon by decreasing said second pressure to a third pressure and additionally stretching said tube a second predetermined distance;

sizing said balloon by increasing said third pressure to a fourth pressure;

crystallizing said PET material of said balloon by decreasing said fourth pressure to a fifth pressure and increasing said first temperature to a second temperature; and cooling said PET material of said balloon by decreasing said second temperature to a third temperature.

2. A method as recited in claim 1 wherein said stretching step is accomplished simultaneously with said pressurizing step.

3. A method as recited in claim 1 wherein said forming step is accomplished over a time interval of approximately ten seconds.

4. A method as recited in claim 1 wherein said thinning step is accomplished over a time interval of approximately five seconds.

5. A method as recited in claim 1 wherein said sizing step is accomplished over a time interval of approximately ten seconds.

6. A method as recited in claim 1 wherein said crystallizing step is accomplished over a time interval of approximately sixty seconds.

7. A method as recited in claim 1 wherein said cooling step is accomplished over a time interval of approximately forty seconds.

8. A method as recited in claim 1 wherein said tube is approximately twelve inches in length and said first predetermined distance in said stretching step is in a range between thirty millimeters and eighty millimeters (30–80 mm).

9. A method as recited in claim 8 wherein said second predetermined distance is in a range between three millimeters and ten millimeters (3–10 mm).

10. A method as recited in claim 1 wherein said first temperature is approximately one hundred and eighty six degrees Fahrenheit (186° F.).

11. A method as recited in claim 1 wherein said second temperature is approximately two hundred and seventy five degrees Fahrenheit (275° F.).

12. A method as recited in claim 1 wherein said third temperature is approximately eighty five degrees Fahrenheit (85° F.).

13. A method as recited in claim 1 wherein said first pressure is approximately one hundred pounds per square inch (100 psi).

14. A method as recited in claim 1 wherein said second pressure is approximately three hundred and twenty pounds per square inch (320 psi).

15. A method as recited in claim 1 wherein said third pressure is approximately thirty five pounds per square inch (35 psi).

16. A method as recited in claim 1 wherein said fourth pressure is approximately three hundred and twenty pounds per square inch (320 psi).

17. A method as recited in claim 1 wherein said fifth pressure is approximately one hundred pounds per square inch (100 psi).

18. A method as recited in claim 1 wherein said PET material for said balloon has an intrinsic viscosity in the range of from 0.66 to 0.78.

* * * * *